United States Patent
Furrer et al.

(10) Patent No.: US 10,821,213 B2
(45) Date of Patent: Nov. 3, 2020

(54) BREAST SHIELD WITH A FLEXIBLE EDGE

(71) Applicant: MEDELA HOLDING AG, Baar (CH)

(72) Inventors: Etienne Furrer, Hagendorn (CH); André Schlienger, Maschwanden (CH); Marcel Muther, Ebikon (CH)

(73) Assignee: MEDELA HOLDING AG, Baar (CH)

( * ) Notice: Subject to any disclaimer, the term of this patent is extended or adjusted under 35 U.S.C. 154(b) by 23 days.

(21) Appl. No.: 15/551,020

(22) PCT Filed: Feb. 9, 2016

(86) PCT No.: PCT/EP2016/052716
§ 371 (c)(1),
(2) Date: Aug. 14, 2017

(87) PCT Pub. No.: WO2016/131678
PCT Pub. Date: Aug. 25, 2016

(65) Prior Publication Data
US 2018/0021492 A1   Jan. 25, 2018

(30) Foreign Application Priority Data
Feb. 20, 2015 (EP) .................................... 15155897

(51) Int. Cl.
*A61M 1/06* (2006.01)

(52) U.S. Cl.
CPC ......... *A61M 1/064* (2014.02); *A61M 2207/00* (2013.01)

(58) Field of Classification Search
CPC .. A61M 1/064; A61M 1/062; A61M 2207/00; E01B 21/04
(Continued)

(56) References Cited

U.S. PATENT DOCUMENTS 4,772,262 A   9/1988 Grant et al.
6,383,164 B1  5/2002 Johansen et al.
(Continued)

FOREIGN PATENT DOCUMENTS

GB   2138686 A * 10/1984 .......... A61M 1/0033
RU   2004123458 A   4/2005
(Continued)

OTHER PUBLICATIONS

Michael J. Troughton, "Handbook of Plastics Joining" (2009), Chapter 4: Spin Welding, Section 4.6, Joint Design.*
(Continued)

*Primary Examiner* — Brandy S Lee
*Assistant Examiner* — Nidal M Hussain
(74) *Attorney, Agent, or Firm* — Marshall, Gerstein & Borun LLP (57) ABSTRACT

A breast shield for a breast pump for pumping human breast milk, comprising a rigid base part having a tubular connecting piece and a funnel that is integrally formed therewith and that expands away from the connecting piece for accommodating a mother's breast. The breast shield includes a flexible collar, which is arranged on the funnel at the end of the funnel facing away from the connection piece, and which is designed to be placed on the mother's breast. The end of the funnel forms a first contact surface, and an end of the collar facing the funnel forms a second contact surface (22), which in a circumferential connecting seam adjoin each other in a blunt way. The funnel has a first wall thickness and the collar has a second wall thickness, wherein said second wall thickness is approximately equal to the first wall thickness. The breast shield can be produced simply and inexpensively, nevertheless allowing a high degree of wearing comfort and a tight fit on the mother's breast.

21 Claims, 7 Drawing Sheets

(58) Field of Classification Search
USPC .................................................. 604/74, 76
See application file for complete search history.

(56) References Cited

U.S. PATENT DOCUMENTS

| | | | |
|---|---|---|---|
| 6,387,072 B1 | 5/2002 | Larsson et al. | |
| 6,673,037 B1* | 1/2004 | Silver | A61M 1/066 604/74 |
| 6,723,066 B2 | 4/2004 | Larsson et al. | |
| 7,413,557 B2 | 8/2008 | Samson et al. | |
| 8,444,596 B2* | 5/2013 | Paterson | A61M 1/0072 604/74 |
| 2006/0106334 A1 | 5/2006 | Jordan et al. | |
| 2006/0111664 A1* | 5/2006 | Samson | A61M 1/06 604/74 |
| 2006/0116632 A1* | 6/2006 | Gillan | A61M 1/064 604/74 |
| 2009/0254029 A1 | 10/2009 | Tashiro et al. | |
| 2010/0324477 A1 | 12/2010 | Paterson et al. | |

FOREIGN PATENT DOCUMENTS

| | | |
|---|---|---|
| WO | WO-03/066133 A1 | 8/2003 |
| WO | WO-2011/035448 A1 | 3/2011 |
| WO | WO-2011/035488 A1 | 3/2011 |

OTHER PUBLICATIONS

Michael J. Troughton, "Handbook of Plastics Joining" (2009), Chapter 4: Spin Welding, Section 4.6, Joint Design. (Year: 2009).*
Russian Search Report for Application No. 2017127963/14(048237), dated Jul. 4, 2019.
International Search Report for International Application No. PCT/EP2016/052716, dated Apr. 20, 2016.

* cited by examiner

FIG. 22

BREAST SHIELD WITH A FLEXIBLE EDGE

The present application is the US national phase of International Application No. PCT/EP2016/052716, filed Feb. 9, 2016, which claims priority to European Application No. 15155897.0, filed Feb. 20, 2015. The priority application, EP 15155897.0, is hereby incorporated by reference.

TECHNICAL FIELD

The present invention relates to a breast shield with a flexible edge for a breast pump for expressing human breast milk.

PRIOR ART

Breast pump systems for expressing human breast milk are well known. They comprise a vacuum pump which is operated manually or by electric motor, at least one breast shield for placing onto the breast, an adapter and a milk collecting container in which the expressed milk is collected. The breast shield is connected to the vacuum pump directly or by means of a suction line such that a cyclically varying negative pressure can be applied to the breast in the breast shield in order to express the milk from the breast. The adapter holds the breast shield and connects it to the vacuum pump or the suction line. The adapter also enables connection to the milk collecting container, either by means of coupling the container on the adapter directly or by means of a milk line.

Known breast shields comprise a funnel and a connection part for connection to the adapter. The funnels are usually realized in the form of a truncated cone, it being possible for them to be rigid or soft. Rigid funnels can also be provided with a soft insert.

The funnel should abut in as sealing a manner as possible against the mother's breast so that an effective pump chamber is able to be formed by the mother's breast and the breast shield. In addition, it should rest pleasantly on the mother's breast in order to enable milk to be expressed in a relaxing manner that is as free of pressure points as possible. In addition, the size and shape of the human mother's breast depends very greatly on the individual and is correspondingly different. Various breast shields which aim to take at least part of said problems into account are known from the prior art.

U.S. Pat. Nos. 6,387,072 and 6,723,066 disclose, for example, a set of breast shields with a rigid shield base and a set of differently sized breast shields which can be inserted into the base. The funnels of the breast shields are realized in the form of a truncated cone, in one embodiment the circumferential edge comprising a recess. Said breast shield can be placed onto the breast such that the recess comes to rest over a sensitive region of the mother's breast or a region which is formed specially anatomically and said region is consequently protected.

US 2006/0116632 proposes arranging the connection part of the breast shield at an angle to a conical funnel.

U.S. Pat. No. 6,673,037 shows a rigid breast shield having a funnel which comprises an elliptical outline. Elevations which act on the breast are present on the inside surface of the funnel.

WO 2011/035448 discloses a relatively small, very flexible breast shield, the opening angle of which adapts to the breast.

U.S. Pat. No. 4,772,262 discloses a soft breast shield with an elliptical opening.

U.S. Pat. No. 7,413,557 describes a breast shield with a rigid funnel and a soft insert injected therein. The insert is pulled further beyond the edge of the funnel as a soft asymmetrical collar. The collar comprises a top surface to be placed on the upper surface of the breast and a bottom surface to be placed on the lower surface of the breast. The disadvantage of said breast shield is that it is too large for small breasts and also does not abut in an optimum manner in the case of specially shaped breasts. In addition, its production is cost-intensive as a relatively large amount of silicone has to be used.

GB 2 138 686 discloses a two-part funnel with a soft, asymmetric part close to the breast. Said part is exchangeable such that it can be selected corresponding to the size of the mother's breast. As, however, it has to be fitted onto the funnel base, the connecting region has a negative effect on the comfort of the mother.

U.S. Pat. No. 8,444,596 proposes injecting a soft lip onto the rigid funnel using a two-component injection molding process.

Although some of the known solutions are already widely accepted by mothers, they still comprise disadvantages with reference to adaptability to the individual sizes and shape of the mother's breast and with reference to abutting against the mother's breast in a sealing manner. One problem is that the breast is not only individually different, but during the expressing process the mother's breast itself also changes. A full breast is hard and large, during expressing it becomes softer and smaller. The pressure sensitivity of the breast tissue and consequently the reaction of the mother to the applied breast shield changes correspondingly. Soft breast shields are more expensive to produce than rigid breast shields. Combined breast shields with a rigid funnel and a soft edge according to the solutions proposed up to now are, however, relatively complex to produce and correspondingly cost-intensive.

DISCLOSURE OF THE INVENTION

It is an object of the invention to create a breast shield which adapts to the mother's breast during the expressing process and is able to be produced in as cost-effective a manner as possible.

The breast shield according to the invention for a breast pump for expressing human breast milk comprises a rigid base part with a tubular connection piece and with a funnel, which is integrally molded in one piece thereon and widens away from the connection piece, for receiving a mother's breast. The breast shield additionally comprises a flexible collar which is arranged on the funnel at an end of the funnel remote from the connection piece and which is realized to be placed on the mother's breast. The named end of the funnel forms a first contact surface. The collar comprises an end which faces the funnel and forms a second contact surface, wherein the first and the second contact surface adjoin one another in an obtuse manner in a circumferential connecting joint. The funnel comprises a first wall thickness in the region of the connecting joint and the collar comprises a second wall thickness which is approximately the same size as the first wall thickness. The first wall thickness and the second wall thickness are preferably precisely the same size, i.e. they are precisely the same thickness.

Said breast shield can be produced in a simple manner. The two contact surfaces are connected by the connecting joint in a way which can only be released by destruction and they form a butt joint. The connection between the two contact surfaces can be effected in the simplest manner by being materially bonded together. The breast shield can be produced in particular using a two-component injection molding process.

In preferred embodiments, the funnel comprises a first opening angle and the collar comprises a second opening angle in the non-loaded state, wherein the second opening angle is smaller than the first opening angle. The collar is preferably inclined inwards with reference to the funnel in the non-loaded state. The collar is preferably pressable outwardly when placed onto the mother's breast and consequently enlarges its receiving opening in an elastic manner. The result of said features individually and in combination with one another is that just a minimum pressing pressure suffices to ensure that the collar of the breast shield abuts in a sealing manner against the breast. The breast shield can also be applied to sensitive breasts in a protecting and gentle manner. In addition, thanks to said features, it also adapts to the changing breast during the expressing process without the mother having to make too many changes to the pressing pressure. In addition, the breast shield is also more easily suitable for small breasts.

In a preferred embodiment, the collar comprises at least, preferably precisely, two planes of symmetry. This increases the fit of the breast shield on the breast and it can be placed in an optimally sealing manner onto the breast. In addition, it can be moved into a position which is adapted to the individual shape and size of the mother's breast. This applies both with the mother standing upright and leaning back.

In preferred embodiments, the collar comprises an end remote from the funnel which end forms a lay-on edge to be placed on the mother's breast, wherein the lay-on edge is a three-dimensional curve which does not extend in one plane. Said breast shield abuts against the breast in an optimum manner thanks to its special three-dimensional curved shape. The special shape makes it possible to place the breast shield in different positions of rotation onto the breast. The mother can choose the position of rotation that is optimum for her and her breast shape. "Optimum" is to be understood within said text in the sense of in the best possible sealing manner and in the best possible pressure-relieving manner. As the mother can rotate the breast shield into another position, it is also possible for her to relieve pressure points. In addition, the breast shield appears to be more ergonomic and feminine with the three-dimensional curve shape. Possible psychological obstacles that the mother may present are removed as a result, which once again increases success during the expressing process.

Not only the funnel but also or as an alternative to this, the lay-on edge comprises at least two or precisely two planes of symmetry. In an optimum embodiment, the lay-on edge comprises a projection, which is in the form of an ellipse, in a plane perpendicular to a longitudinal axis of the breast shield. In alternative embodiments, said projection is a closed traverse with rounded corners and sides that are inclined inwards. The overall impression is flower-shaped.

The collar is preferably a truncated cone and even more preferably a straight circular truncated cone. The same applies to the funnel. The combination of said shape with a non-even three-dimensional curve as a lay-on edge results in a breast shield with an optimum fit. As a result, the breast shield fits snugly against the mother's breast in a constantly increasing and zone-wise elastic manner.

In preferred embodiments, the collar in its non-loaded state comprises a constant opening angle in the direction of the longitudinal center axis of the breast shield, at least as far as into a region of an end of the collar that is remote from the funnel. This means that the lay-on edge can definitely be at a different angle and, for example, is able to be inclined more severely outward in order to form an enlarged contact surface.

In preferred embodiments, the first wall thickness is increased in the region of the connecting joint in comparison to an adjoining wall thickness of the funnel and/or the second wall thickness of the collar is increased in the region of the connecting joint in comparison to an adjoining wall thickness of the collar. Said thickening of the wall thicknesses in the region of the connecting joint leads to the breast shield nevertheless being sturdy and the collar being fastened in a sufficiently tear-proof manner on the funnel. In addition, said thickening forms a haptic element for improving handling. The breast shield can be produced with relatively little material consumption thanks to the thickening. This results in a light breast shield which is consequently pleasant for the mother to use. In addition, this reduces the production costs.

Both wall thicknesses in the region of the connecting joint are preferably realized in an increased manner in comparison to their adjoining wall thicknesses or they are realized in a thicker manner.

The wall thickness of the funnel in the region of the first wall thickness and/or the wall thickness of the collar in the region of the second wall thickness increase in a stepless manner or in a step. Depending on the embodiment, both can comprise stepless increases or they can both be increased in one step. In another embodiment, one increase is effected in a stepless manner and the other is effected in a step.

The connecting joint preferably does not extend in one plane. The breast-side end of the funnel preferably also comprises a non-even three-dimensional curve. The connecting joint preferably comprises a constant form. In other embodiments, however, it extends in an inconstant manner. The connecting joint can also extend in one plane.

The breast shield preferably consists simply of said two regions: i.e. of the integral base part and the integral collar.

Further embodiments are provided in the dependent claims.

BRIEF DESCRIPTION OF THE DRAWINGS

Preferred embodiments of the invention are described below by way of the drawings which serve purely for explanation and are not to be deemed restrictive, in which:

FIG. 8b shows a variant to FIG. 8a;

FIG. 9b shows a variant to FIG. 9a;

FIG. 10b shows a variant to FIG. 10a;

DESCRIPTION OF PREFERRED EXEMPLARY EMBODIMENTS

Figure 1:
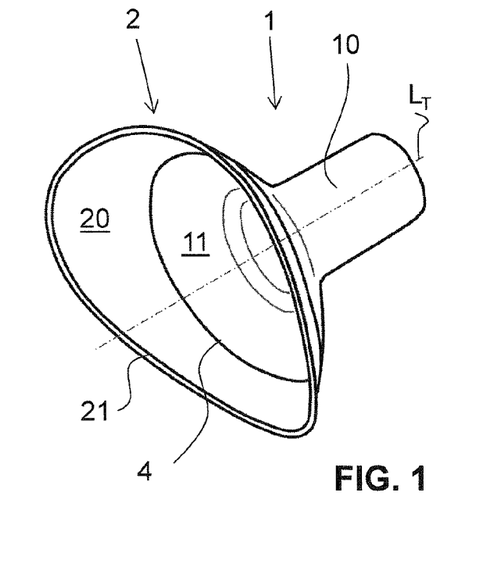
FIG. 1 shows a perspective representation of a first embodiment of a breast shield according to the invention.
Figure 2:
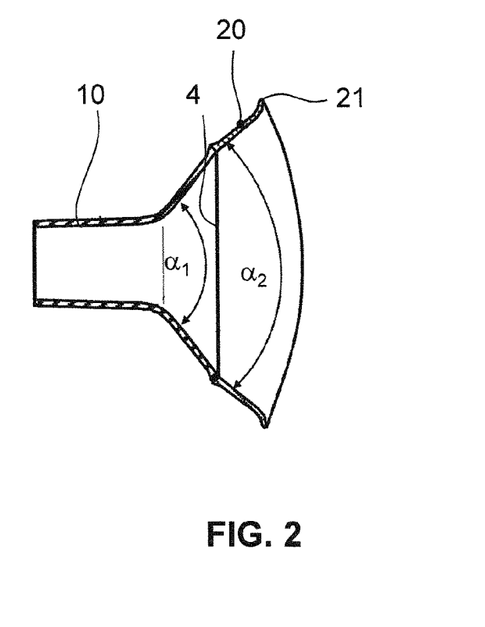
FIG. 2 shows a longitudinal section through the breast shield according to FIG. 1.
Figure 3:
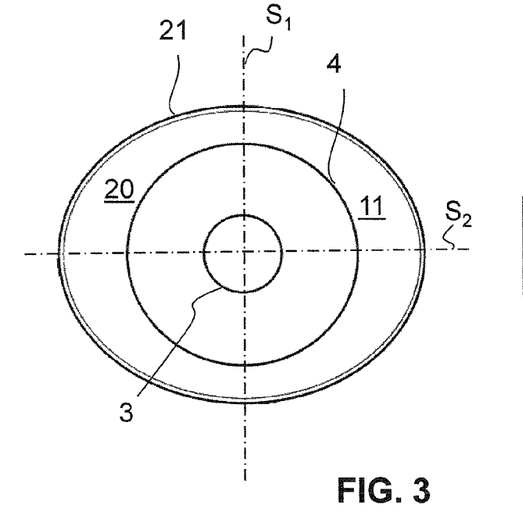
FIG. 3 shows a view of a first embodiment of the breast shield close to the breast according to FIG. 1 with one form of a connecting joint.

FIGS. 1 to 3 show a first exemplary embodiment of a breast shield according to the invention. It comprises an inflexible or rigid base part 1 and a flexible and preferably soft collar 2 that is integrally molded thereon. The base part 1 and the collar 2 together form a channel or a passage 3 so that a negative pressure which is generated cyclically by a vacuum pump is applied to the mother's breast and expressed milk is able to flow from the mother's breast into a milk collecting container.

The base part 1 and the collar 2 are preferably produced from plastics material and preferably consist of different materials. The base part 1 is preferably produced from polypropylene (PP) and the collar 2 from a thermoplastic elastomer (TPE). They are preferably produced together in one piece in a two-component injection molding process.

The base part 1 comprises a tubular connecting piece 10 for connection to an adapter part (not shown here) of a breast pump system. These types of adapters or coupling parts are adequately familiar. They hold the breast shield and connect the breast shield to the vacuum pump and the milk collecting container.

The connecting piece 10 merges integrally into a funnel 11 which widens from the connecting piece 10 toward the breast. The funnel 11, in the examples described here, is a straight circular truncated cone. It preferably comprises a first opening angle $\alpha_1$ of between 90° and 120° and is preferably 105°.

The rigid funnel 11, on its inside surface and/or on its outside surface, preferably does not comprise any elevations or indentations. Its inside surface and its outside surface are consequently preferably realized in a smooth manner. This results in optimum sliding with the skin. The smooth outside surface, however, can be realized in a rough manner in order to obtain sufficient grip for the mother. It can also be provided with haptic elements which facilitate the rotational positioning of the breast shield for the mother.

Figure 8A:
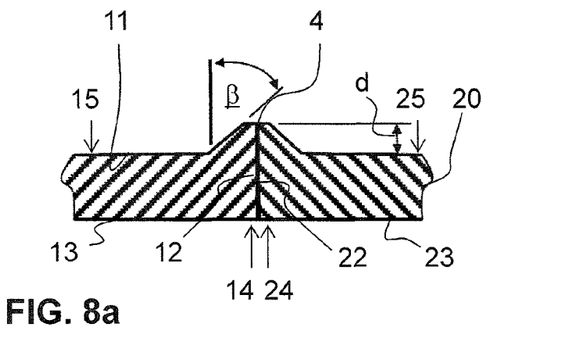
FIG. 8a shows a section through the region of a connecting joint with wall thicknesses of the funnel and of the collar in a first embodiment.

The funnel 11 comprises an end which is remote from the connecting piece 10 and forms a first contact surface 12. Said first contact surface 12 can be seen in FIG. 8.

The soft collar 2 comprises a basic body 20 with an end which is remote from the breast and is connected to the funnel 11 by means of a connecting joint 4 and an end which is close to the breast and forms a lay-on edge 21 to be placed onto the mother's breast.

In said example the basic body 20 comprises the form of a straight circular truncated cone. It ends close to the breast in a three-dimensional curve which is closed per se, i.e. in a curve which does not lie in one plane. Said three-dimensional curve forms the lay-on edge 21.

The lay-on edge 21 is preferably realized in a flat manner so that it abuts not only in a linear manner but also flatly against the breast. This can be achieved, for example, by thickening the lay-on edge 21 in comparison to the remaining wall of the collar 2 or the lay-on edge 21, as shown in FIG. 2, can be realized curved to the outside.

The three-dimensional curve of the lay-on edge 21 can be formed in an arbitrary manner. In said example, its projection perpendicular to the longitudinal centre axis $L_T$ of the breast shield is an ellipse, as can be seen in FIG. 3. The projection consequently comprises precisely two axes of symmetry $S_1$ and $S_2$. The lay-on edge 21 and consequently the collar 2 comprise precisely two planes of symmetry which include the two axes of symmetry and which extend perpendicular to the drawing plane. Said planes of symmetry are consequently also provided with the references $S_1$ and $S_2$.

The collar 2 can comprise an arbitrary form. Its lay-on edge 21 can be a three-dimensional curve or an even curve. Its basic body 20 can have the form, for example, of a straight cone with an elliptical basic form or a crooked cone. It can also have a different form, e.g. an asymmetric form. However, it preferably comprises at least two axes or planes of symmetry. However, the three-dimensional curves shown here with elliptical projections centred onto the axis $L_T$ are preferred.

The circular-truncated-cone-shaped basic body 20 comprises an opening $\alpha_2$ which is preferably smaller than the opening angle $\alpha_1$ of the funnel 11. The second opening angle $\alpha_2$ is preferably between 10° and 40° smaller than $\alpha_1$ at an angle $\alpha_1$ of 105°. $\alpha_2$ is preferably approximately 80°.

The collar 2 in the non-loaded state is preferably inclined inwards in relation to the funnel 11. If the basic body 20 is a truncated cone with an elliptical outline, its second opening angle $\alpha_2$ over at least part of its circumference, preferably over the entire circumference, is smaller than the opening angle $\alpha_1$ of the funnel 11. The opening angles $\alpha_1$, $\alpha_2$ of both the funnel 11 and of the collar 2 preferably remain unchanged in the direction of the longitudinal centre axis $L_T$ of the breast shield and consequently along the fall lines of the inside surfaces of the funnel 11 or of the collar 2.

The first end of the collar 2 facing the funnel 11 comprises the same form as the adjacent end of the funnel 11. Here it is consequently circular. It forms a second contact surface 22 which can be seen in FIG. 8.

Figure 8B:
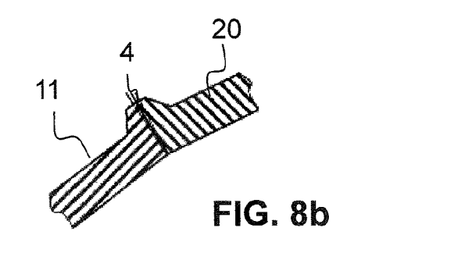
Figure 9A:
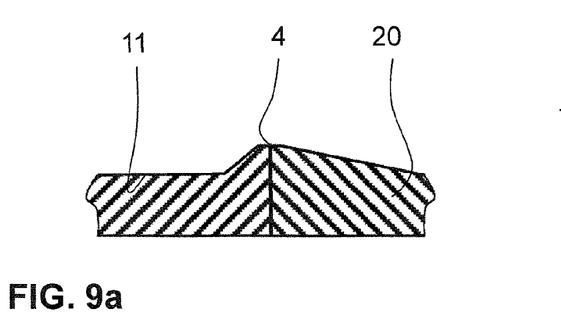
FIG. 9a shows a section through the region of a connecting joint with wall thicknesses of the funnel and of the collar in a second embodiment.
Figure 9B:
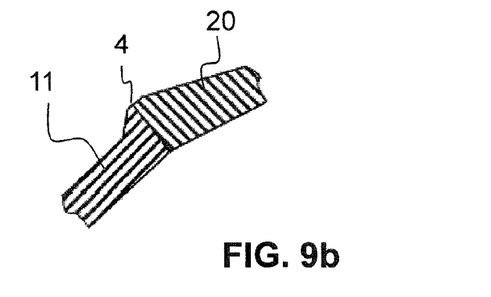
Figure 10A:
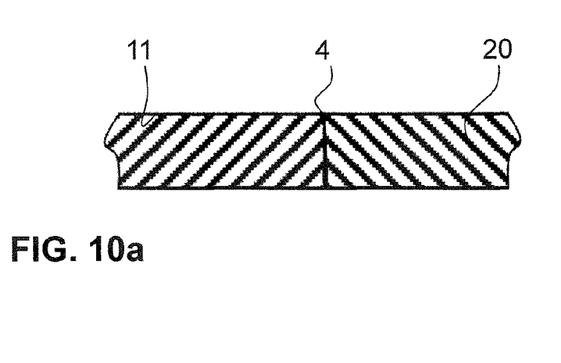
FIG. 10a shows a section through the region of a connecting joint with wall thicknesses of the funnel and of the collar in a third embodiment.
Figure 10B:
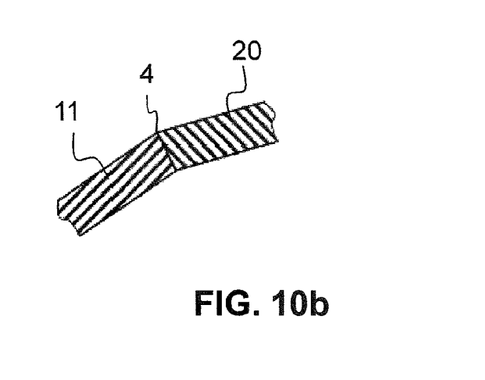

FIG. 8a is not in line with the images according to FIG. 2. In FIG. 2 the collar 2 is inclined inwards and the connection or the joint formed by the collar 2 and the funnel 11 is effected at an angle. Said angle is preferably between 10° and 30°. In FIGS. 8a, 9a and 10a, in contrast, the connection is in one plane and the two inside surfaces 13, 23 of the funnel 11 and of the collar 2 are in alignment with one another. A lineal connection is possible, the angled connection being preferred. Said angled connection is shown in FIGS. 8b, 9b and 10b.

As shown in FIG. 2, the funnel 11 is realized in a thicker manner in the region of the first contact surface 12 than in its adjoining wall. The same applies to the second contact surface 22 of the collar 2. Said situation is shown enlarged in FIG. 8a.

The angle of inclination β of the step at which the two walls merge into the two contact surfaces 12, 22, is preferably between 30° and 70° and in an even more preferable manner is 45°. The increase d in the outside surface is between 0.5 and 1.5 mm in said connecting region. The wall thicknesses of the funnel 11 and of the collar 2 are the same size at least in the connecting region. In the examples in FIGS. 10a and 10b, this also applies in the adjoining region.

The basic wall thickness of the funnel 11, i.e. the wall thickness of the predominant part of the funnel 11, is provided with the reference 15 and the basic wall thickness of the collar 2 is provided with the reference 25. The thickened first wall thickness of the funnel 11 has the reference 14 and the thickened second wall thickness of the collar 2 has the reference 24. In FIG. 8a, the inside surface 13 of the funnel 11 and the inside surface 23 of the collar 2 are realized in a flat manner in alignment with one another. This is, as described above, not the case in the embodiments shown here.

FIGS. 9a and 9b show an alternative realization of the connecting region. In this case, the funnel 11 is simply thickened in a step-shaped and consequently inconstant manner. The collar 2 is thickened in a continuous manner.

The embodiments according to FIGS. 10a and 10b do not have any thickening in the region of the connection.

Figure 4:
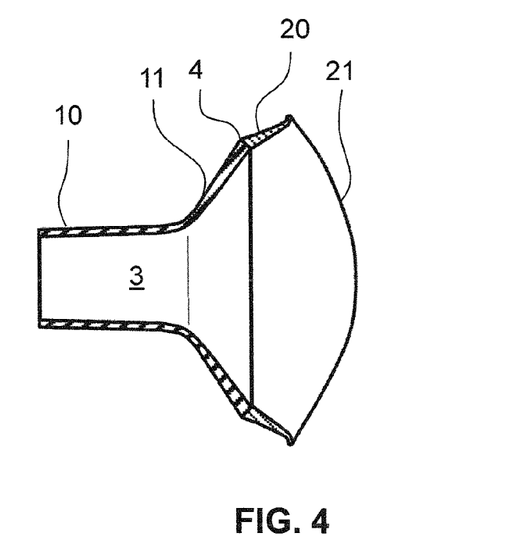
FIG. 4 shows a longitudinal section through a second embodiment of a breast shield according to the invention.
Figure 5:
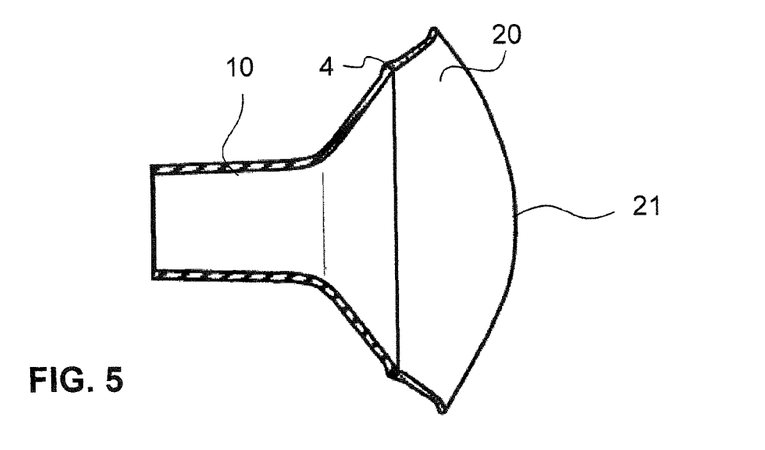
FIG. 5 shows a longitudinal section through a third embodiment of a breast shield according to the invention.
Figure 6:
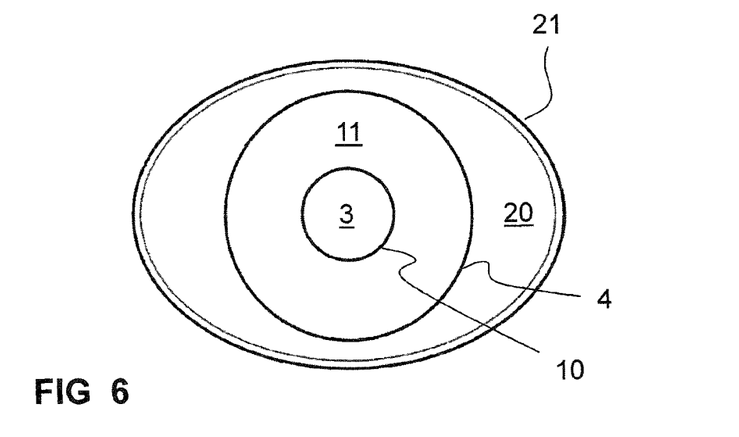
FIG. 6 shows a view of the breast shield close to the breast according to FIG. 5.
Figure 7:
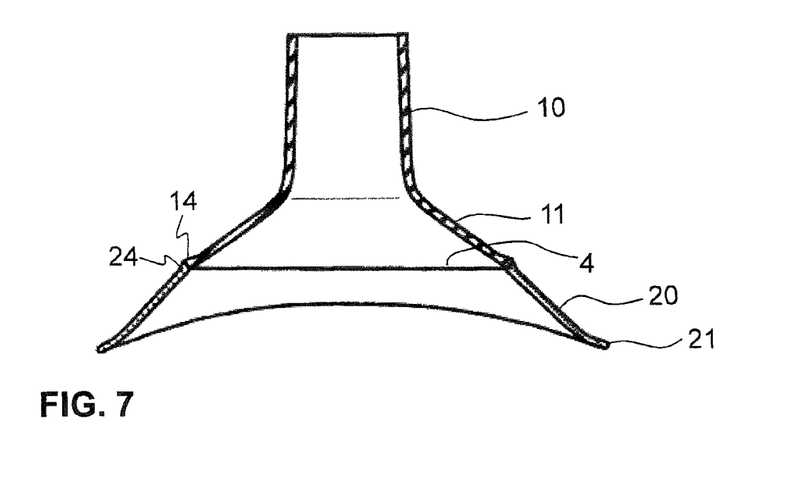
FIG. 7 shows another longitudinal section through the breast shield according to FIG. 5.

In the exemplary embodiment according to FIG. 4, the funnel 11 and the collar 2 become thicker in a constant manner. In addition, the collar 2 is realized in a shorter manner than in the first exemplary embodiment. In the first example, the collar 2 comprises approximately the same length as the funnel 11 or it comprises at least more than half the length of the funnel 11. In the example according to FIG. 4, its length is a maximum of half the length of the funnel 11, measured in each case along the outside surface. The same applies to the exemplary embodiment according to FIGS. 5 to 7. In the exemplary embodiment according to FIGS. 5 to 7, the ellipse of the lay-on edge 21 is realized in a flatter manner than the one in the first exemplary embodiment.

Figure 11:
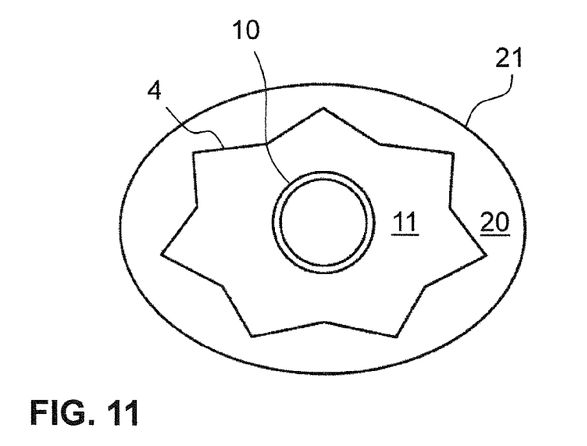
FIG. 11 shows a view of a breast shield with a second embodiment of a form of a connecting joint.
Figure 12:
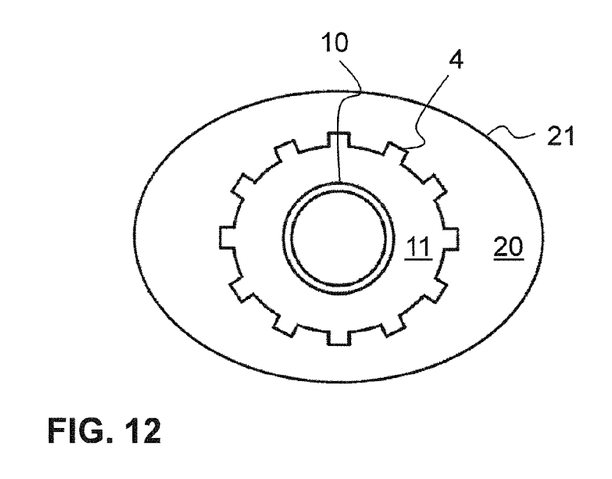
FIG. 12 shows a view of a breast shield with a third embodiment of a form of a connecting joint.

FIGS. 11 and 12 show variants of the connecting joint 4. In the above-described embodiments, the connecting joint 4 is a circle. In the embodiment according to FIG. 11 it is inconstant and is in the form of a star In FIG. 12 it is also inconstant. In this case it is meander-shaped or tooth-shaped. The advantage of said forms is that the bond between the collar 2 and the funnel 11 is strengthened. Further forms are also possible.

Figure 13:
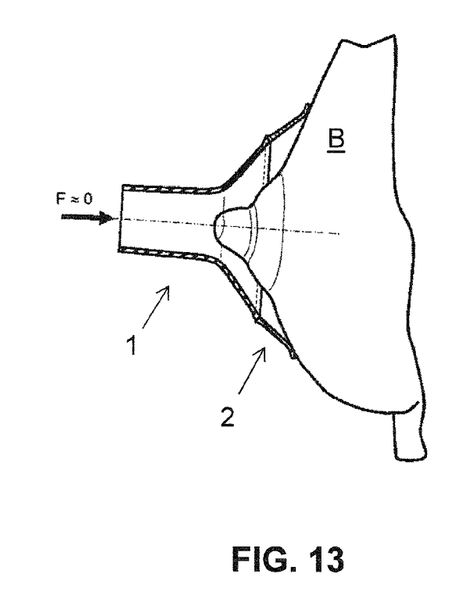
FIG. 13 shows a view from the side of a longitudinal section through a breast shield according to the invention prior to being placed onto a mother's breast.
Figure 14:
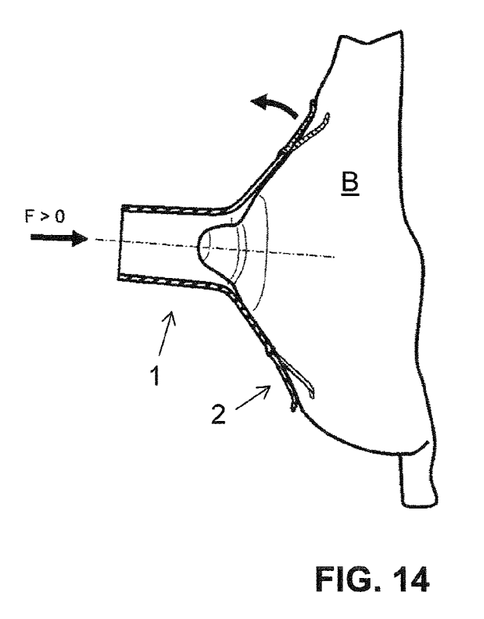
FIG. 14 shows the longitudinal section through the breast shield according to FIG. 13 after being placed onto a mother's breast.
Figure 15:
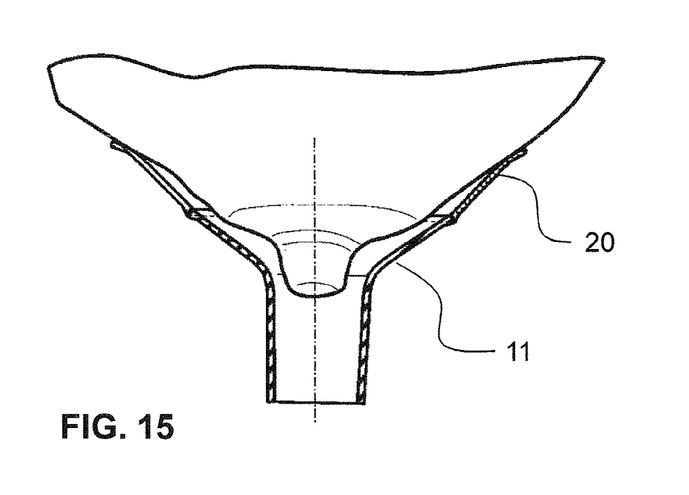
FIG. 15 shows a view from above of a longitudinal section through the breast shield according to FIG. 13 prior to being placed onto the mother's breast.

FIGS. 13 to 15 show that the collar 2 is flexibly adapted to the breast B and its opening angle when pressed onto the breast B is increased. In FIGS. 13 and 15 there is still no pressing pressure F present and the collar 2 is still not loaded. The collar 2 is still inclined inwards. In FIG. 14, the breast shield is pressed against the breast B at a force F that is greater than nought. The collar 2 is bent away from the breast B in the direction of the curved arrow and the opening angle is increased. The collar 2 abuts against the breast B with its entire circumference in a sealing manner, but without any painful pressure points and without excessive pressure. Thanks to the inwardly directed inclination of the collar in the non-loaded state, a small amount of pressure is sufficient so that the breast shield abuts in a sealing manner and adapts to the anatomy of the breast.

The length of the collar 2 is preferably dimensioned such that it abuts against the breast over its entire length when in use. As a result it is prevented from deforming under the negative pressure applied. The nipple and the areola of the breast preferably lie in the rigid funnel such that when the vacuum is applied, it is not possible for the breast shield to deform in said region.

FIGS. 16 to 22 show two further exemplary embodiments. The funnel 11 and the basic body 20 of the collar 2 are once again a straight circular truncated cone. The collar 20, however, comprises a lay-on edge 21 in the form of a three-dimensional curve, the projection of which perpendicular to the longitudinal centre axis $L_T$ of the breast shield produces a traverse which is closed per se.

Figures 16, 17, 18:
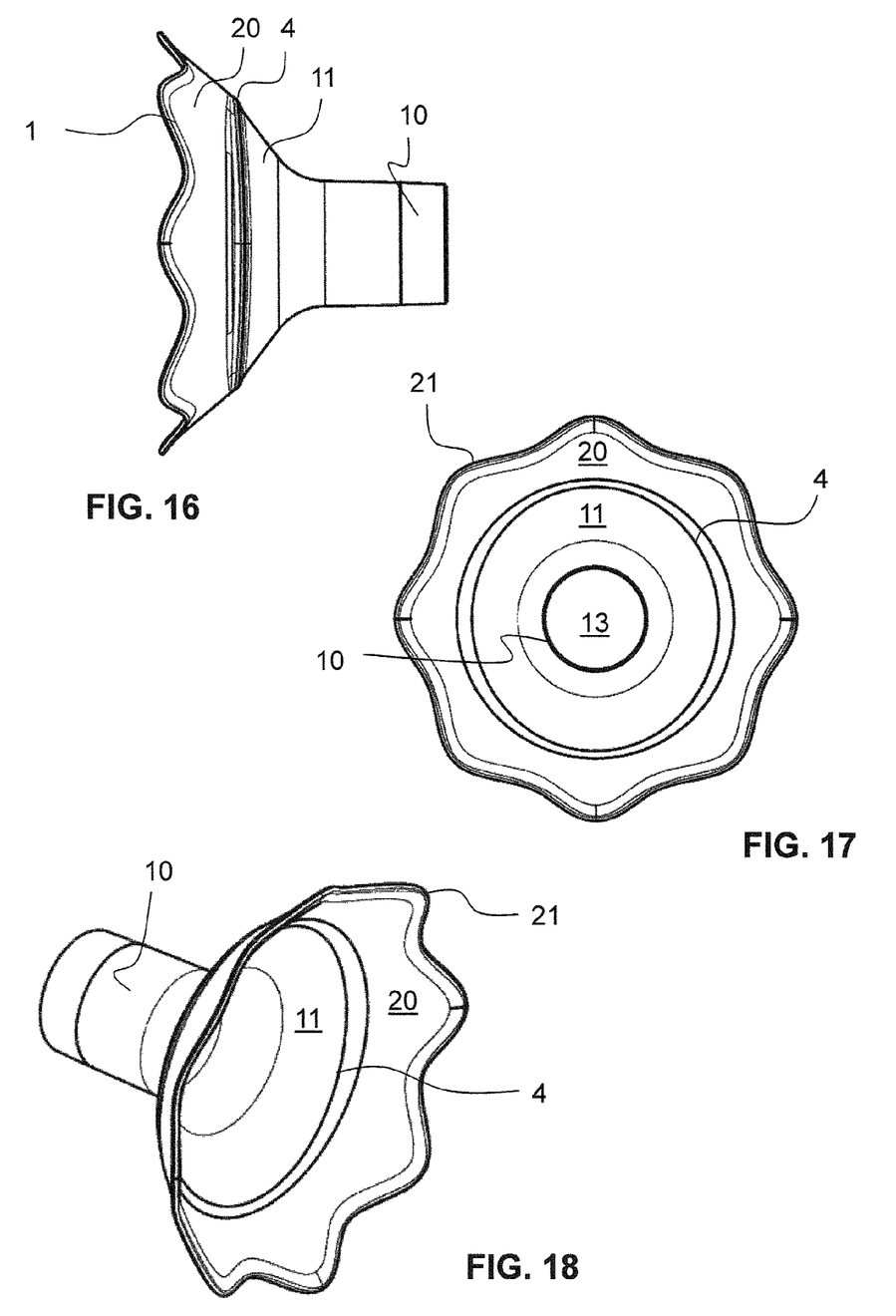
FIG. 16 shows a side view of a further embodiment of a breast shield according to the invention.
FIG. 17 shows a view close to the breast of the breast shield according to FIG. 16.
FIG. 18 shows a perspective representation of the breast shield according to FIG. 16.
Figure 19:
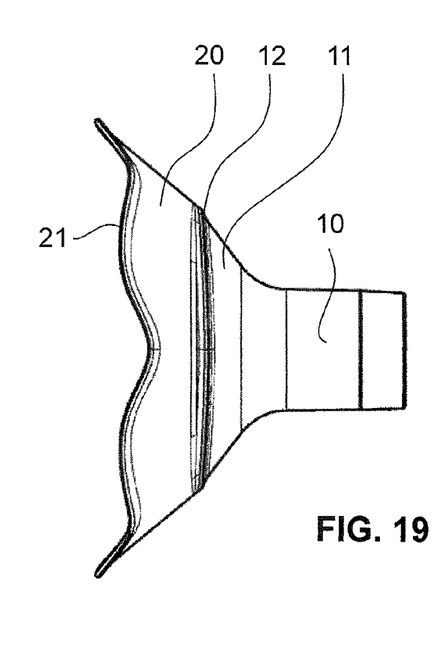
FIG. 19 shows a first side view of a further embodiment of a breast shield according to the invention.
Figure 20:
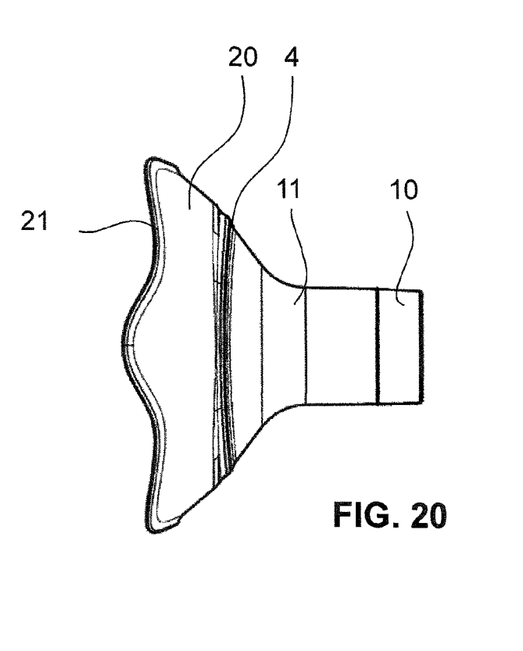
FIG. 20 shows a second side view of the breast shield according to FIG. 19.
Figure 21:
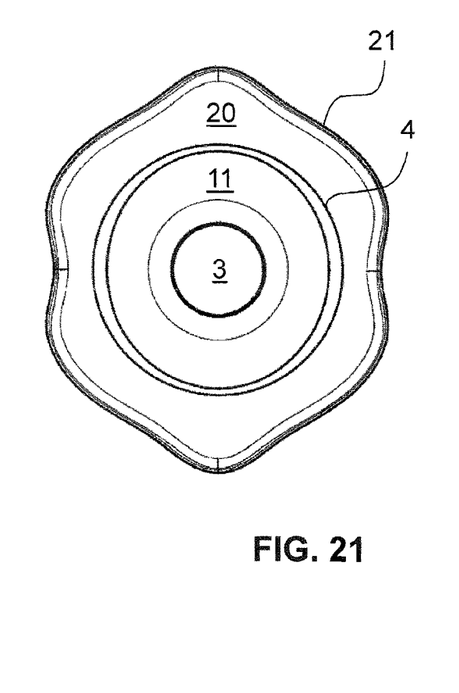
FIG. 21 shows a view remote from the breast of the breast shield according to FIG. 19
Figure 22:
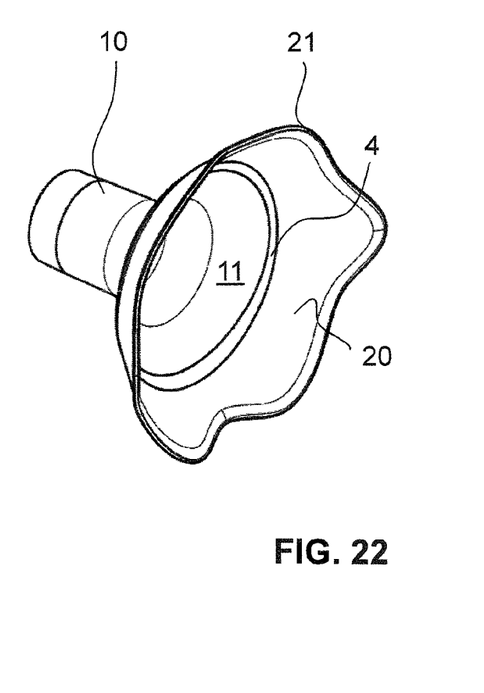
FIG. 22 shows a perspective representation of the breast shield according to FIG. 19.

The lay-on edge 21 in the embodiment according to FIGS. 16 to 18 is an octagonal traverse which is closed per se with rounded corners and sides which bend inwards. Its projection consequently comprises three axes of symmetry and its enveloping form is a circle. The lay-on edge and the collar comprise three corresponding planes of symmetry.

The lay-on edge 21 in the embodiment according to FIGS. 19 to 22 is a hexagonal traverse which is closed per se with rounded corners and sides which bend inwards.

The lay-on edges 21 according to said two exemplary embodiments have a flower-shaped appearance. Said two variants can be provided with the different connecting joints and wall thicknesses already mentioned, in particular according to FIGS. 8a to 10b. The collar 2 is preferably also inclined inwards in each case or, as shown in FIGS. 8a, 9a and 10a, it can be injected on in a straight line.

The breast shield according to the invention can be produced in a simple and cost-efficient manner and nevertheless is very comfortable to wear and can be placed in position on the mother's breast in a sealing manner.

What is claimed is:

1. A breast shield for a breast pump for expressing human breast milk, wherein the breast shield comprises a rigid base part with a tubular connection piece and with a funnel for receiving a mother's breast, the funnel having an end and the funnel being integrally molded in one piece on the tubular connection piece and widening away from the tubular connection piece, wherein the breast shield additionally comprises a flexible collar which is arranged on the funnel at the end of the funnel remote from the tubular connection piece and which is realized to be placed onto the mother's breast, wherein the end of the funnel forms a first contact surface, wherein the collar comprises an end which faces the funnel and forms a second contact surface;

wherein the funnel comprises a first opening angle, wherein the collar comprises a second opening angle in a non-loaded state, the second opening angle being smaller than the first opening angle;

wherein the first contact surface and the second contact surface adjoin one another in an obtuse manner in a circumferential connecting joint, the connecting joint being a butt joint;

wherein the funnel comprises a first wall thickness in a region of the connecting joint and the collar comprises a second wall thickness in the region of the connecting joint;

wherein the first wall thickness and the second wall thickness are approximately the same size, and wherein the first wall thickness is increased in a region of the connecting joint in comparison to an adjoining wall thickness of the funnel; and wherein the connecting joint formed by the collar and the funnel is effected at a joint angle, so that the second opening angle being smaller than the first opening angle is provided.

2. The breast shield according to claim 1, wherein the first wall thickness and the second wall thickness are precisely the same size.

3. The breast shield according to claim 1, wherein the collar is inclined inwards with reference to the funnel in the non-loaded state.

4. The breast shield according to claim 1, wherein the collar is pressable outwardly when placed onto the mother's breast and consequently a receiving opening of the collar is enlargeable.

5. The breast shield according to claim 1, wherein the collar comprises at least two planes of symmetry.

6. The breast shield according to claim 1, wherein the collar comprises an end remote from the funnel which forms a lay-on edge to be placed onto the mother's breast, wherein the lay-on edge is a three-dimensional curve which does not extend in one plane.

7. The breast shield according to claim 6, wherein a projection of the lay-on edge in a plane perpendicular to a longitudinal axis of the breast shield is an ellipse.

8. The breast shield according to claim 6, wherein a projection of the lay-on edge in a plane perpendicular to a longitudinal axis of the breast shield is a traverse which is closed per se and has rounded corners and sides which incline inwards.

9. The breast shield according to claim 1, wherein the collar is a straight truncated cone.

10. The breast shield according to claim 1, wherein the collar in the non-loaded state comprises a constant opening angle in a direction of a longitudinal center axis of the breast shield, at least as far as into a region of an end of the collar remote from the funnel.

11. The breast shield according to claim 1, wherein the connecting joint extends in one plane.

12. The breast shield according to claim 1, wherein the connecting joint comprises an inconstant form.

13. The breast shield according to claim 1, wherein the funnel is a circular truncated cone and the collar comprises an end which is remote from the funnel and forms a lay-on edge to be placed onto the mother's breast, wherein said lay-on edge comprises a form which deviates from a circle.

14. The breast shield according to claim 1, wherein the second wall thickness of the collar is increased in the region of the connecting joint in comparison to an adjoining wall thickness of the collar.

15. The breast shield according to claim 1, wherein the collar is a straight circular truncated cone.

16. The breast shield according to claim 1, wherein the collar comprises precisely two planes of symmetry.

17. The breast shield according to claim 1, wherein the joint angle is between 10° and 30°.

18. The breast shield according to claim 1, wherein the collar is molded on the funnel.

19. A breast shield for a breast pump for expressing human breast milk, wherein the breast shield comprises a rigid base part with a tubular connection piece and with a funnel for receiving a mother's breast, the funnel having an end and the funnel being integrally molded in one piece on the tubular connection piece and widening away from the tubular connection piece, wherein the breast shield additionally comprises a flexible collar which is arranged on the funnel at the end of the funnel remote from the tubular connection piece and which is realized to be placed onto the mother's breast, wherein the end of the funnel forms a first contact surface, wherein the collar comprises an end which faces the funnel and forms a second contact surface;

wherein the first contact surface and the second contact surface adjoin one another in an obtuse manner in a circumferential connecting joint, the connecting joint being a butt joint;

wherein the funnel comprises a first wall thickness in a region of the connecting joint and the collar comprises a second wall thickness in the region of the connecting joint;

wherein the first wall thickness and the second wall thickness are approximately the same size and wherein the first wall thickness is increased in the region of the connecting joint in comparison to an adjoining wall thickness of the funnel; and wherein the connecting joint formed by the collar and the funnel is effected at an angle.

20. The breast shield according to claim 19, wherein the angle is between 10° and 30°.

21. A breast shield for a breast pump for expressing human breast milk, wherein the breast shield comprises a rigid base part with a tubular connection piece and with a funnel for receiving a mother's breast, the funnel having an end and the funnel being integrally molded in one piece on the tubular connection piece and widening away from the tubular connection piece, wherein the breast shield additionally comprises a flexible collar which is arranged on the funnel at the end of the funnel remote from the tubular connection piece and which is realized to be placed onto the mother's breast, wherein the end of the funnel forms a first contact surface, wherein the collar comprises an end which faces the funnel and forms a second contact surface, wherein the first contact surface and the second contact surface adjoin one another in an obtuse manner in a circumferential connecting joint, the connecting joint being a butt joint;

wherein the funnel comprises a first wall thickness in a region of the connecting joint and the collar comprises a second wall thickness in the region of the connecting joint, wherein the first wall thickness and the second wall thickness are approximately the same size and wherein the first wall thickness is increased in the region of the connecting joint in comparison to an adjoining wall thickness of the funnel, and wherein the collar comprises an opening angle, wherein the collar is inclined with this opening angle inwards with reference to the funnel in the non-loaded state and wherein the opening angle of the collar is constant in a direction of a longitudinal center axis of the breast shield, at least as far as into a region of an end of the collar that is remote from the funnel.

* * * * *